US 7,536,263 B2

(12) United States Patent
Shim et al.

(10) Patent No.: US 7,536,263 B2
(45) Date of Patent: *May 19, 2009

(54) ROBUST GENOTYPING METHOD USING DNA CHIP HAVING DISCRIMINATING PROBE AND AMPLICON PROBE IMMOBILIZED THEREON AND DNA CHIP USED THEREIN

(75) Inventors: Hyeong-sop Shim, Gyeonggi-do (KR); Jong-min Kim, Gyeonggi-do (KR); Ji-young Oh, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 437 days.

This patent is subject to a terminal disclaimer.

(21) Appl. No.: 11/019,011

(22) Filed: Dec. 21, 2004

(65) Prior Publication Data

US 2005/0142599 A1    Jun. 30, 2005

(30) Foreign Application Priority Data

Dec. 26, 2003    (KR) .................. 10-2003-0097806

(51) Int. Cl.
*G06F 19/00* (2006.01)
*C12Q 1/68* (2006.01)

(52) U.S. Cl. ............................... 702/19; 435/6
(58) Field of Classification Search .......... None
See application file for complete search history.

(56) References Cited

U.S. PATENT DOCUMENTS 6,027,880 A    2/2000   Cronin et al.
6,300,063 B1   10/2001  Lipshutz et al.
6,303,301 B1   10/2001  Mack

FOREIGN PATENT DOCUMENTS

KR    1020030020232 A    3/2003
KR    1020030072709 A    9/2003

OTHER PUBLICATIONS

Cronin et al. Cystic Fibrosis Mutation Detection by Hybridization to Light-Generated DNA Probe Arrays. Human Mutation vol. 7, pp. 244-255 (1996).*
Nieminen et al. Equivalent Clinical Effectiveness of Old and New Models of Easyhaler. Current Therapeutic Research vol. 60, pp. 73-80 (1999).*
Hosmer, D. W. and Stanley Lemeshow. Applied Logistic Regression: Wiley Series in Probability and Statistics, Second Edition, John Wiley & Sons Inc., 1989, pp. 1-30.

* cited by examiner

*Primary Examiner*—John S Brusca
(74) *Attorney, Agent, or Firm*—Cantor Colburn LLP

(57) ABSTRACT

Provided is a genotyping method. The genotyping method includes using a DNA chip on which just an optimal probe set is immobilized, the optimal probe sets composed of a discriminating probe which perfectly matches a mutant type gene or a wild type gene for each of at least one identified mutation site in each of at least one amplicon contained in a sample and an amplicon probe having a sequence which perfectly matches a region excluding a nucleotide sequence at a mutation site in each amplicon and is absent from the other amplicons, in order to identify which one of a wild type gene and a mutant type gene is present in each mutation site. In this genotyping method, the number of probes used can be reduced and reliability of genotyping results can be increased.

17 Claims, 6 Drawing Sheets

ROBUST GENOTYPING METHOD USING DNA CHIP HAVING DISCRIMINATING PROBE AND AMPLICON PROBE IMMOBILIZED THEREON AND DNA CHIP USED THEREIN

BACKGROUND OF THE INVENTION

This application claims the priority of Korean Patent Application No. 10-2003-0097806, filed on Dec. 26, 2003, in the Korean Intellectual Property Office, the disclosure of which is incorporated herein in its entirety by reference.

1. Field of the Invention

The present invention relates to a robust method of identifying whether a target nucleic acid is a wild type or a mutant type using a DNA chip and a DNA chip used therein.

2. Description of the Related Art

The most common genotyping method is to identify sequences using sequencing machine. This method is accurate but is unsuitable for genotyping a number of samples simultaneously and leads to a low yield.

Recent disclosures of DNA chips that can simultaneously identify various genotypes at different positions, such as U.S. Pat. Nos. 6,027,880 and 6,300,063, are attracting a lot of interest. The DNA chips disclosed in the patents utilize tiled arrays of from 9 to 25-mer oligonucleotide probes at non-mutation sites and A, C, G, and T at mutation sites. Since all possible base combinations are used for a tiled array of probes mobilized at or close to mutation sites, the number of required probes increases four times whenever one more tiled array site is required.

However, such a tiled array includes redundant probes for an identified target nucleic acid. In addition, the tiled array method cannot be applied to detect mutations, for example, by insertion or deletion. Since a tiled array includes numerous probes having similar sequences and a fixed length, it is difficult to accurately analyze the results of genotyping a particular locus using such a tiled array, and then, the manufacturing costs of DNA chips rise. For example, if the hybridization intensity of a wild-perfect match probe or a mutant-perfect match probe is lower than the hybridization intensity of the other mismatch probes, a genotyping error occurs and thus, it is not possible to prove a cross-hybridization effect. Also, the fixed length of the probes in the tiled array hinders the optimal hybridization with a particular nucleic acid.

SUMMARY OF THE INVENTION

The present invention provides a genotyping method that is immune from errors in discrimination and utilizes a minimum number of probes that have various lengths.

The present invention also provides a DNA chip used in the above genotyping method.

According to an aspect of the present invention, there is provided a genotyping method comprising using a DNA chip on which just an optimal probe set is immobilized, the optimal probe sets composed of a discriminating probe which perfectly matches a mutant type gene or a wild type gene for each of at least one identified mutation site in each of at least one amplicon contained in a sample and an amplicon probe having a sequence which perfectly matches a region excluding a nucleotide sequence at a mutation site in each amplicon and is absent from the other amplicons, in order to identify which one of a wild type gene and a mutant type gene is present on each mutation site.

According to another aspect of the present invention, there is provided a DNA chip on which optimal probe sets only are immobilized, the optimal probe sets of a discriminating probe which perfectly matches a mutant type gene or a wild type gene and an amplicon probe having a sequence which perfectly matches a region excluding a nucleotide sequence at mutation site in each amplicon and is absent from the other amplicons.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
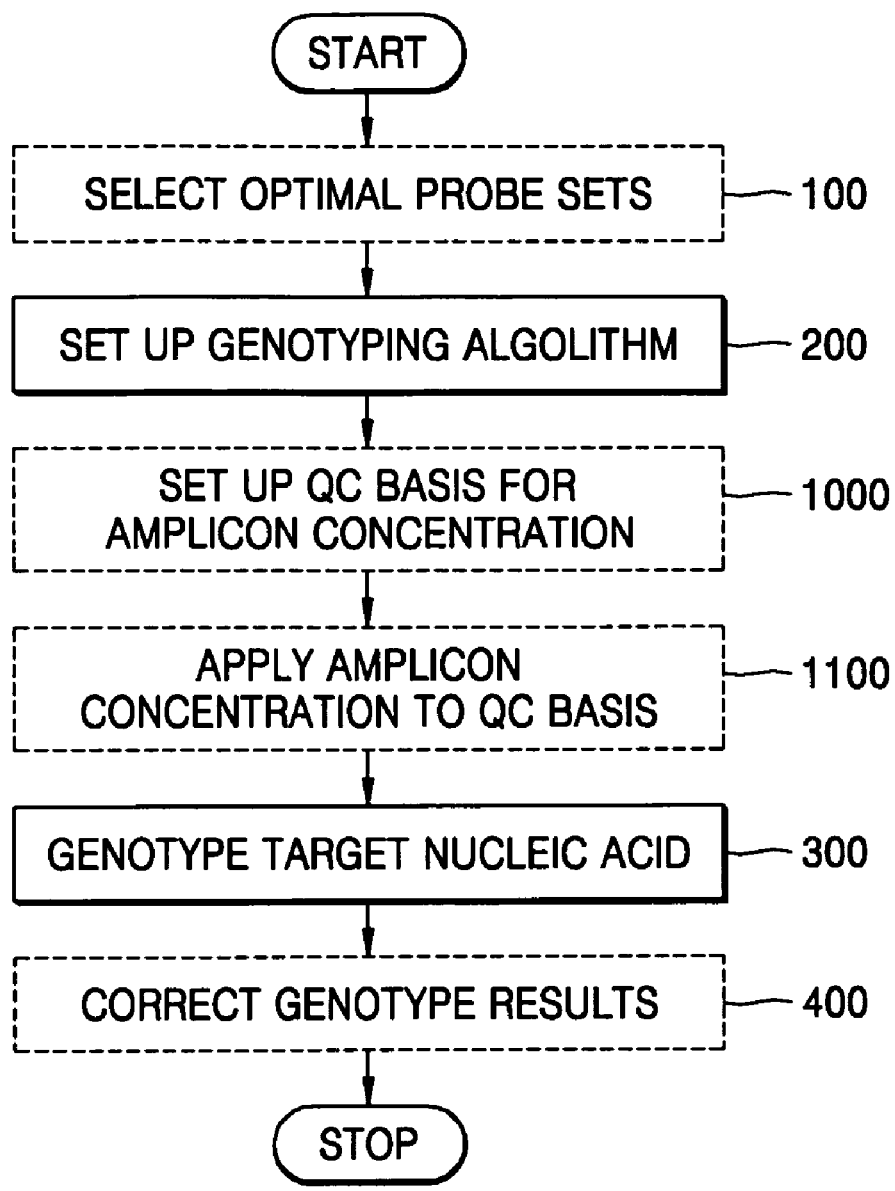
FIG. 1 is a flowchart of a genotyping method according to an embodiment of the present invention.

According to an embodiment of the present invention, there is provided a genotyping method comprising using a DNA chip on which just an optimal probe set is immobilized, the optimal probe sets composed of a discriminating probe which perfectly matches a mutant type gene or a wild type gene for each of at least one identified mutation site in each of at least one amplicon contained in a sample and an amplicon probe having a sequence which perfectly matches a region excluding a nucleotide sequence at a mutation site in each amplicon and is absent from the other amplicons, in order to identify which one of a wild type gene and a mutant type gene is present on each mutation site. At least two replicates of optimal probe sets may be immobilized for each mutation site on the DNA chip.

The genotyping method may include setting up a genotyping algorithm using data obtained from hybridization of an identified standard nucleic acid on the DNA chip, and genotyping an unknown target nucleic acid by substituting an input vector that is calculated from hybridization of the target nucleic acid on the DNA chip into the genotyping algorithm. The genotyped results may be corrected based on cross-hybridization data of the probe set for each mutation site.

The genotyping method may further comprise setting up a basis for sample quality control (QC) regarding whether each amplicon has been satisfactorily amplified, using the hybridization intensity of the identified standard nucleic acid to an amplicon probe obtained from hybridization of the standard nucleic acid to the DNA chip; and applying the hybridization intensity of the unknown target nucleic acid to an amplicon probe obtained from hybridization of the target nucleic acid to the DNA chip, to the above QC basis to exclude an amplicon which fails the QC from determination on whether a mutation is present, prior to the genotyping of the target nucleic acid. The QC basis may be a determination algorithm of amplicon concentration regarding whether the concentration of each amplicon in the sample is greater than a set-up value based on the data obtained from the hybridization of the identified standard nucleic acid to the DNA chip. In the application to the QC basis, the amplicon concentration may be determined by substituting an input vector that is calculated from data obtained from hybridization of the unknown target nucleic acid to the DNA chip into the determination algorithm. If the amplicon concentration is not more than the set-up value, the amplicon may be excluded from the determination on whether a mutation is present.

According to another embodiment of the present invention, there is provided a DNA chip on which optimal probe sets only are immobilized, the optimal probe sets of a discriminating probe which perfectly matches a mutant type gene or a wild type gene and an amplicon probe having a sequence which perfectly matches a region excluding a nucleotide sequence at mutation site in each amplicon and is absent from the other amplicons.

Embodiments of a genotyping method and a DNA chip used therein according to an embodiment of the present invention will be described with reference to the appended drawings. This invention may, however, be embodied in many different forms and should not be construed as being limited to the embodiments set fourth herein; rather, these embodiments are provided so that this disclosure will be complete, and will fully convey the concept of the invention to those skilled in the art. The scope of the present invention is defined only by the appended claims. In the drawings, like reference numerals are used to refer to like elements throughout.

Throughout the specification, the term "DNA chip" refers to a microarray of a number of nucleic acid probes. Nucleic acids refers to nucleotides that include pyrimidine bases, including cytosine, thymine, and uracil, and purine bases, including adenine and guanine, and polymers (also referred to as polynucleotides) or oligomers (also referred to as oligonucleotides) of the nucleotides. Examples of DNA chips include cDNA chips with at least 500 bp probes and oligonuclotide chips with polygonucleotide probes.

The term "standard nucleic acid" used throughout the specification refers to a nucleic acid that has an identified genotype. The term "target nucleic acid" refers to a nucleic acid of interest that has an unidentified genotype. The target nucleic acid may be an oligonucleotide or polynucleotide of RNA or DNA. The term "probe" refers to a nucleic acid used to genotype the target nucleic acid. Hereinafter, a probe having a sequence which perfectly matches a region excluding a nucleotide sequence at a mutation site in each amplicon and is absent from the other amplicons will be referred to as an amplicon probe (ap). A probe which perfectly matches a mutant type gene will be referred to as a mutant type probe (mp) and a probe which perfectly matches a wild type gene will be referred to as a wild type probe (wp). A probe which perfectly matches a mutant type gene or a wild type gene for determining whether a mutation is present will be referred to as a discriminating probe (dp).

In the flowcharts, blocks outlined by dashed lines denote optional processing operations.

Referring to FIG. 1, a robust genotyping method according to an embodiment of the present invention includes setting up a genotyping algorithm (operation 200) and genotyping a target nucleic acid (operation 300). Optionally, the genotyping method according to an embodiment of the present invention may further include selecting optimal probe sets (operation 100) before the setting up a genotyping algorithm (operation 200) and correcting the genotyped results (operation 400) after the genotyping a target nucleic acid (operation 300). Optionally, the genotyping method according to an embodiment of the present invention may further include setting up an amplicon concentration QC basis (operation 1000) before and after the setting up a genotyping algorithm (operation 200) and applying the hybridization intensity of the target nucleic acid to the amplicon concentration QC basis (operation 1100) before and after genotyping a target nucleic acid (operation 300), to exclude a mutant amplicon which fails the QC from the subject to be determined.

In the genotyping method according to an embodiment of the present invention, a DNA chip on which only optimal probe sets are immobilized, the optimal probe sets of a discriminating probe which perfectly matches a mutant type gene or a wild type gene for each mutation site to be analyzed and an amplicon probe having a sequence which perfectly matches a region excluding a nucleotide sequence at mutation site in each amplicon and is absent from the other amplicons is used. Therefore, there is no need to lay unnecessary probes on the chip. In addition, the results are easy to interpret, and errors resulting from cross-hybridization can be easily corrected, and the manufacturing costs of the DNA chip are low. The genotyping method according to an embodiment of the present invention may be applied to mutants, for example, by insertion or deletion. Moreover, since an amplicon probe specific to each amplicon is used in the genotyping method according to an embodiment of the present invention, only amplicons which are present at a concentration equal to or higher than the set-up value can be analyzed, thus increasing the reliability of the analytical results of a genotype. The genotyping method according to an embodiment of the present invention will be described step by step.

Optimal Probe Set Selection

Figure 2:
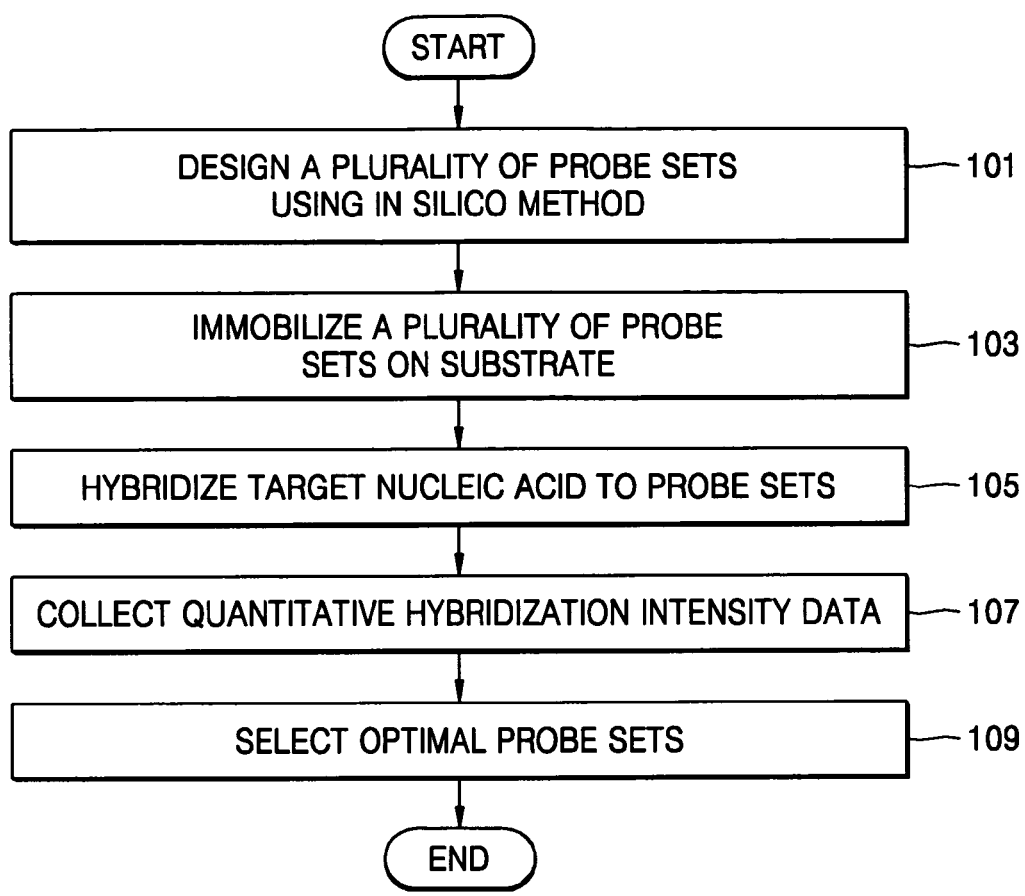
FIG. 2 is a detailed flowchart of the operation of screening optimal probe sets in the genotyping method according to an embodiment of the present invention.

FIG. 2 is a detailed flowchart of the screening of optimal probe sets (operation 100) in FIG. 1. First, probes are designed using an in silico method (operation 101). For this, information on mutants of a nucleic acid to be analyzed must be collected using a known nucleic acid database, such as NCBI or DDBJ, or based on papers. Next, an amplicon including the mutation site is determined. Throughout the specification, the term "amplicon" refers to an amplifying unit which is repeatedly amplified using an amplifying method known in the art, for example, a polymerase chain reaction (PCR) or its amplified product. The amplicon used in the genotyping method may have at least one mutation site.

After the determination of amplicon, information on mutants in each amplicon is collected. Next, a plurality of mp probes or wp probes (i.e, dp probes) are designed for each mutation site on each amplicon and a plurality of ap probes are designed for each amplicon (operation 101). The lengths of ap and dp probes may be the same or different. In other words, there is no limitation to the length of the ap and dp probes provided that they are the same strand. An ap probe selected from the plurality of ap amplicons designed for each amplicon and a dp probe selected from the plurality of dp probes designed for each mutation site to be analyzed in each amplicon are combined to obtain ap-dp sets. Whether a sequence having a predetermined number (for example, nine) of same continuous nucleotides are present in the other amplicon sequences or not may be an additional basis for selecting an ap. The ap selected based on the additional basis is thermodynamically simulated to calculate a binding force between the ap and the standard amplicon. Only the ap having a binding force of a predetermined value or more is selected. Visual OMP 3 program available from DNA Software Corp., for example, may be used for the simulation. The following basis can be considered for selecting a dp. First, in order to discriminate whether the sample to be analyzed is homo-wild type nucleic acid or hetero type nucleic acid, an mp is advantageously used as a dp, since both homo wild type nucleic acid and hetero type nucleotide include a wild type gene but the sequences are different at a mutation site in a hetero type nucleic acid (gain of signal approach). Similarly, in order to discriminate whether the sample to be analyzed is homo mutant type nucleic acid or hetero type nucleic acid, a wp is advantageously used as a dp. At this time, whether a sequence having a predetermined number (for example, nine) of same continuous nucleotides are present in the other amplicon sequences or not may be an additional basis for selecting a dp. The dp selected on the additional basis is thermodynamically simulated to estimate a binding force between the dp and the wild type amplicon and a binding force between the dp and the mutant type amplicon, respectively. When a perfect match occurs, the dp having a binding force of a predetermined value or more is selected in such an order that the dp has a greater difference between a binding force with the mutant type amplicon and a binding force with the wild type amplicon. Visual OMP 3 program available from DNA Software Corp., for example, may be used for the simulation.

Then, the ap-dp sets are immobilized on a substrate to form a complete chip for screening optimal probe sets (operation 103). The immobilization of the ap-dp sets on the substrate may be achieved by one of various methods that are known to those of ordinary skill in the field. As an example, the ap-dp sets may be immobilized on the chip according to a method disclosed in Korean Patent Application No. 2001-53687 filed by the same applicant as the present invention, incorporated herein by reference in its entirety.

Next, a target nucleic acid is hybridized on the chip that is manufactured to screen optimal probe sets (operation 105). This hybridization process may be carried out by one of various methods that are known to those of ordinary skill in the field. After hybridization, quantitative hybridisation intensity data are collected by means of a scanner (operation 107). A number of quantitative hybridization intensity data are collected using a plurality of optimal probe set screening chips. Finally, optimal ap-dp sets for the respective amplicons are selected based on the quantitative hybridization intensity data (operation 109). Equation (1) below, as a non-limited example, may be used to select the optimal ap-dp sets for the respective mutation sites.

$$\{Mean(\ln(r^{WS}))-2SD(\ln(r^{WS}))/\sqrt{N^{WS}}\}-\{Mean(\ln(r^{HS}))+2SD(\ln(r^{HS}))/\sqrt{N^{HS}}\} \quad (1)$$

In equation (1) above, N denotes the number of times hybridization of the target nucleic acid has been performed; $r^{WS}$ is the ratio between the hybridization intensity of a wild type standard nucleic acid to the ap and the hybridization intensity of the wild type standard nucleic acid to the dp; $r^{HS}$ is the ratio between the hybridization intensity of a mutant type standard nucleic acid to the ap and the hybridization intensity of the mutant type standard nucleic acid to the dp; and Means and SD denote the mean values and standard deviation of N ln(r) values, respectively, which are obtained by hybridizing the standard nucleic acid to the DNA chip N times. The median of N ln(r) values instead of the mean value may be used.

A probe pair having the largest value among the values calculated using equation (1) is selected as an optimal ap and dp (x) probe pair for a mutation site x in a given amplicon. The process is repeated for each mutation site to obtain optimal ap and dp pairs for each mutation site. From the obtained pairs, a discriminating probe composed of an optimal ap for the given amplicon and an optimal dp for each mutation site is selected.

The optimal probe set may be selected using a method disclosed in Korean Patent Application No. 02-118771 filed on Mar. 6, 2002 by the same applicant as the present invention, incorporated herein by reference in its entirety.

It will be appreciated that this process of screening out the optimal probe sets may be not conducted when there is a known optimal probe set for each mutation site to be analyzed in a given amplicon.

Genotyping Algorithm Set up

After the optimal probe sets for the respective mutation sites to be analyzed in a given amplicon are selected according to the procedure of FIG. 2, a genotyping algorithm is set up.

Figure 3:
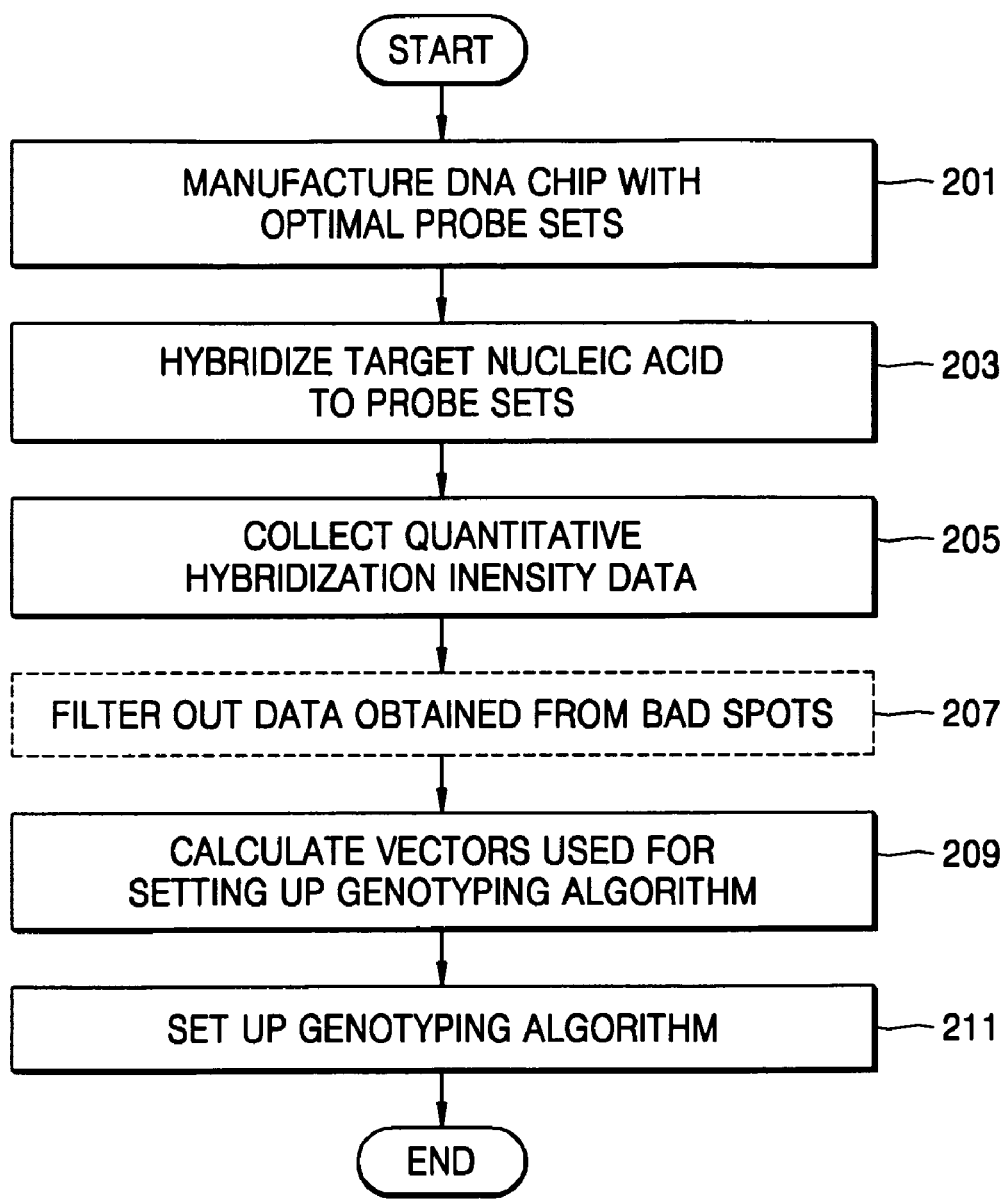
FIG. 3 is a detailed flowchart of the operation of setting up a genotyping algorithm.

Referring to FIG. 3, which is a detailed flowchart of the setting up of the genotyping algorithm (operation 200) in FIG. 1, a DNA chip is manufactured by arranging the optimal probe sets for the respective mutation sites to be analyzed in a given amplicon in a microarray (operation 201). This DNA chip may be manufactured by the same method applied to the manufacture of the optimal probe set screening chip. It is preferable that at least two identical optimal probe sets are arranged for each of the mutation sites to be analyzed in a given amplicon for quality control (QC) and quality assurance (QA). It is more preferable that ap probes form a separate group and the dp probes form a separate group. In the group of the ap probes, the amplification degrees of the target nucleic acid can be compared with each other. In the group of the dp probes, when the target nucleic acid having a mutation at a specific site is hybridized to the dp probes, only a relevant dp probe has a sufficiently strong binding force. It is most preferable that three dp probes for each mutant type to be analyzed in a given amplicon and three ap probes selected for each amplicon are arranged on the DNA chip in terms of QC, QA, and costs.

Next, after the target nucleic acid is hybridized on the chip (operation 203), quantitative hybridization intensity data are collected by means of a scanner (operation 205). After hybridization, the quantitative hybridization intensity data is collected and, finally, the chip is washed.

Data obtained from bad spots among the quantitative hybridization intensity data may be filtered out (operation 207). Criteria for bad spot discrimination include an effective spot diameter cut-off value, an effective spot intensity cut-off value, etc., which can be calculated based on a large amount of statistical data. In an embodiment of the present invention, spots that have a larger diameter than an effective spot diameter are considered as bad spots for statistical data analysis and thus, eliminated.

Next, vectors for the genotyping algorithm are calculated using the quantitative hybridization intensity data (operation 209). These vectors may be calculated using the Hodge-Lehman (H-L) estimation that is a typical method applied in nonparametric statistics to increase the robustness of the genotyping algorithm. The vectors used to set up the genotyping algorithm in the present invention include ratio components and/or intensity components.

Ratio components are calculated as follows.

The ratio between the hybridization intensity of a nucleic acid to an amplicon probe ($ap_i$) and the hybridization intensity of the nucleic acid to a discriminating probe ($dp_j$) is calculated for all of the probe sets, where i×j=n, as expressed in equation (2) below.

$$r_{ij} = \frac{\text{Hybridization Intensity to } ap_i}{\text{Hybridization Intensity to } dp_j} \quad (2)$$

After calculating the ratios $r_{ij}$ for all of the probe sets, the ratios $r_{ij}$ are arranged in ascending order, for example, $r(1) \leq r(2), \ldots, r(n-1) \leq r(n)$, and the median, $r(m)$, is selected from among the ratios.

For example, when three ap probes and three dp probes are arranged at a mutation site, the ratios for a total of nine ap-dp probe sets are calculated and arranged in ascending order, i.e., $r(1) \leqq, \ldots, \leqq r(5) \leqq, \ldots, r(9)$, and $r(5)$ is selected as the median $r(m)$.

The natural logarithm of the median $r(m)$, expressed in equation (3) below, is used as a ratio component.

$$M = \text{Ratio component} = \ln(r(m)) \quad (3)$$

Alternatively, the common logarithm (log) of the median $r(m)$ instead of the natural logarithm (ln) may be used as the ratio component.

The use of the median results in a genotyping algorithm that is more robust to experimental errors than using the arithmetic means of the hybridization intensities of the probes for each mutation site. For example, when the hybridization intensity of dp3 greatly deviates from the hybridization intensities of dp1 and dp2, as in Table 1 below, calculating the median using H-L estimation as a ratio component leads to a result that is more robust to experimental errors than calculating the arithmetic means.

TABLE 1

| Probe name | Hybridization intensity |
| --- | --- |
| ap1 | 948 |
| ap2 | 870 |
| ap3 | 1071 |
| dp1 | 74 |
| dp2 | 73 |
| dp3 | 1363 |

Intensity components are calculated as follows.

A first method involves multiplying the hybridization intensities of each of the ap-dp probe sets to obtain the products $a_{ij}$, as expressed in equation (4) below, where i×j=n.

$$a_{ij} = ap_i \times dp_j \quad (4)$$

After calculating the products $a_{ij}$ for all of the ap-dp probe sets, the median $a(m)$ among the products $a_{ij}$ is selected using H-L estimation in the same manner as described above.

The natural logarithm of the median $a(m)$ is divided by two to obtain an intensity component A, as expressed in equation (5) below.

$$A = \text{Intensity component} = \ln(a(m))/2 \quad (5)$$

A second method involves taking the larger of the hybridization intensities of each of the ap-dp probe sets, as expressed in equation (6) below.

$$m_{ij} = \max(ap_i, dp_j) \quad (6)$$

The median $m(m)$ is selected from among $m_{ij}$ and the common logarithm of the median $m(m)$ is used as an intensity component A, as expressed in equation (7) below.

$$A = \text{Intensity component} = \log(m(m)) \quad (7)$$

The common logarithm may be applied instead of the natural logarithm in equation (5). The natural logarithm may be applied instead of the common logarithm in equation (7).

Operations 203 through 209 are performed using a plurality of chips to obtain a plurality of ratio components M and intensity components A.

The vectors consisting of the ratio components M and the intensity components A, which are obtained based on the hybridization intensity data according to the above-described methods, are used to set up the genotyping algorithm (operation 211).

To set up the genotyping algorithm, an MA plot with the Y and X axes parameterized by the ratio (M) and intensity (A) components, respectively, is obtained.

Figure 4:
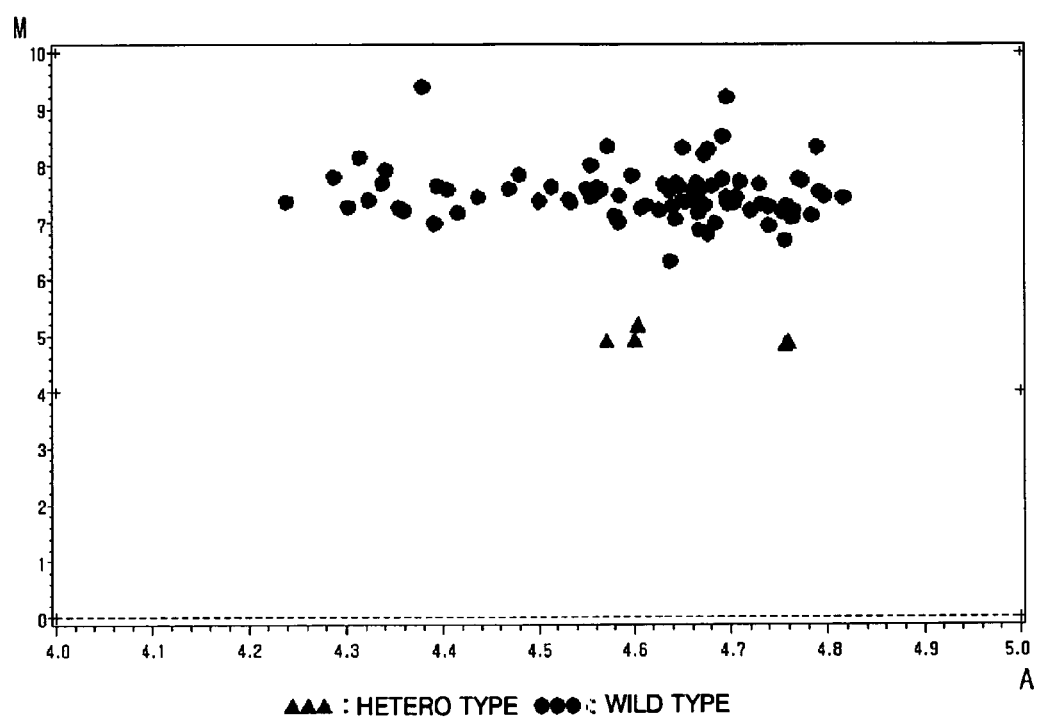
FIG. 4 is a graph of ratio component (M) versus intensity component (A) used in setting up a genotyping algorithm for position 13 of exon 1 (E01-13) of HNF-1α gene.

FIG. 4 is an MA plot used in setting up a genotyping algorithm for position 13 of exon 1 (E01-13) of HNF-1α gene. Since a mutant of HNF-1α gene is present not in a hetero form, but in a homo form, a mutant type gene is used as a dp. The MA plot of FIG. 4 was obtained through the following processes.

E01-13 mutant is a deletion type mutant in which a sequence in a wild type gene sense strand, GCCCCCT (SEQ ID No. 1) is modified to a sequence GCCCCT (SEQ ID No. 2). E01-13 mp (gaagGCCCCTggac: SEQ ID No. 3) is used as a dp for E01-13 and E01 ap (GCTCCGAGGACGAGAC: SEQ ID No. 4) is used as an ap for E01-13. An array of probes were immobilized on a glass substrate to manufacture a complete chip such that three ap probes and three dp probes were positioned side by side on the glass substrate. A spotting solution of E01-13 mp and E01 ap probes with amine groups dispersed in a hydrogel prepared from a polyethyleneglycol (PEG) derivative with epoxy groups was used to manufacture the chip. The spotting solution was spotted onto an aminated surface of the glass substrate using a biorobot printer (PixSys 5500, Cartesian Technologies InC., CA, U.S.A.) and incubated in a humid incubator at 37° C. for 4 hours. To control background noise, amine groups in a non-spotting region of the glass substrate were reacted to gain a negative charge, which prevents standard nucleic acids from binding to the non-spotting region of the substrate, and then stored in a drier.

The standard nucleic acid was fluorescently labelled. Available fluorescent materials include fluorescein isothiocyanate (FITC), fluorescein, Cy3, Cy5, Texas Red, and the like. In the experiment regarding the MA plot of FIG. 4, Cy3-dUTP was used as the fluorescent material.

The standard nucleic acid was hybridized to the probes as follows. A 20 nM standard nucleic acid solution in 0.1% 6×SSPET (saline sodium phosphate EDTA buffer containing 0.1% Trition X-100) was reacted with the chip at 37° C. for 16 hours. Then, the chip was washed with 0.05% 6×SSPET and 0.05% 3×SSPET, respectively, for 5 minutes, dried at room temperature for 5 minutes, and scanned using an Axon scanner (GenePix 4000B, Axon Instrument Inc., CA., U.S.A.). The resulting scanning data were analyzed using software (GenePix Pro 3.0, Axon Instrument Inc., CA., U.S.A.) to calculate the ratio and intensity components and plot FIG. 4. The scanning data were obtained through hybridization with a wild type standard nucleic acid using 80 chips and through hybridization with a mutant type standard nucleic acid using 5 chips.

When the ratio component M remains constant as the intensity component A varies, as in FIG. 4, a genotyping algorithm is set up using only the ratio component M. The genotyping algorithm may be set up using logistic regression coefficients a and b predicted by logistic regression.

However, when the ratio component M has a strong dependence on the intensity component A, for example, when the ratio component M decreases with decreasing intensity component A, the genotyping algorithm may be set up according to one of the following methods. In one method, a set of probes with the ratio components that decrease with decreasing intensity components is disregarded when calculating the logistic regression coefficients a and b using logistic regression. In another method, the genotyping algorithm may be set up based on a 2-dimensional vector matrix of probes ratio components and intensity components. However, the former is preferred to the latter in consideration of inherent great intensity variations in the DNA chip.

Genotyping

After the genotyping algorithm is set up through the above processes, genotyping is performed on a target nucleic acid of interest. Input vectors for the genotyping algorithm set up in operation 211 are calculated based on the results of a test performed on the target nucleic acid using the DNA chip.

Figure 5:
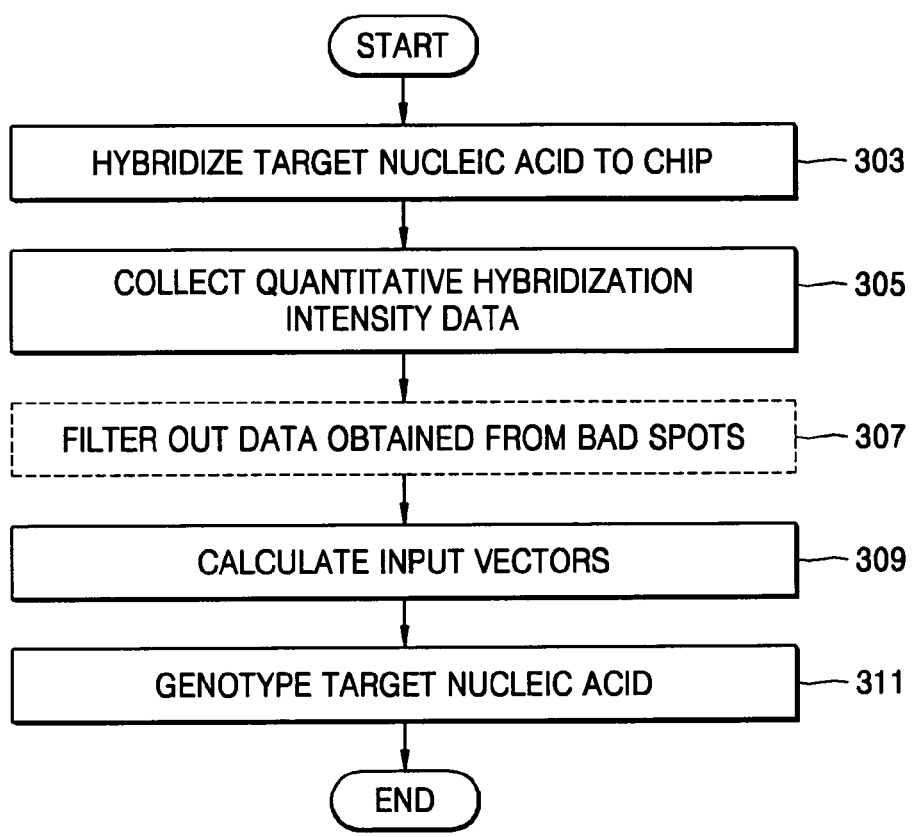
FIG. 5 is a detailed flowchart of the operation of genotyping.

FIG. 5 is a detailed flowchart of a genotyping process. Up to the operation of calculating the input vectors is performed in the same manner as in operation 211 of setting up the genotyping algorithm. In particular, the target nucleic acid of interest is hybridized to the chip with which the genotyping algorithm has been set up (operation 303). Next, quantitative hybridization intensity data regarding the target nucleic acid are collected (operation 305). Optionally, data obtained from bad spots may be filtered out from the quantitative hybridization intensity data (operation 307).

Next, the input vectors for the genotyping algorithm are calculated based on the quantitative hybridization intensity data (operation 309). Ratio components are calculated using the H-L estimation as in operation 211. When an MA plot is required as in operation 211, intensity components as well as the ratio components are calculated.

The genotype of the target nucleic acid is identified using the genotyping algorithm with the input vectors (operation 311). The genotyped results for the target nucleic acid and the standard nucleic acid may be plotted together on the same MA graph for comparative visual identification.

Figure 6:
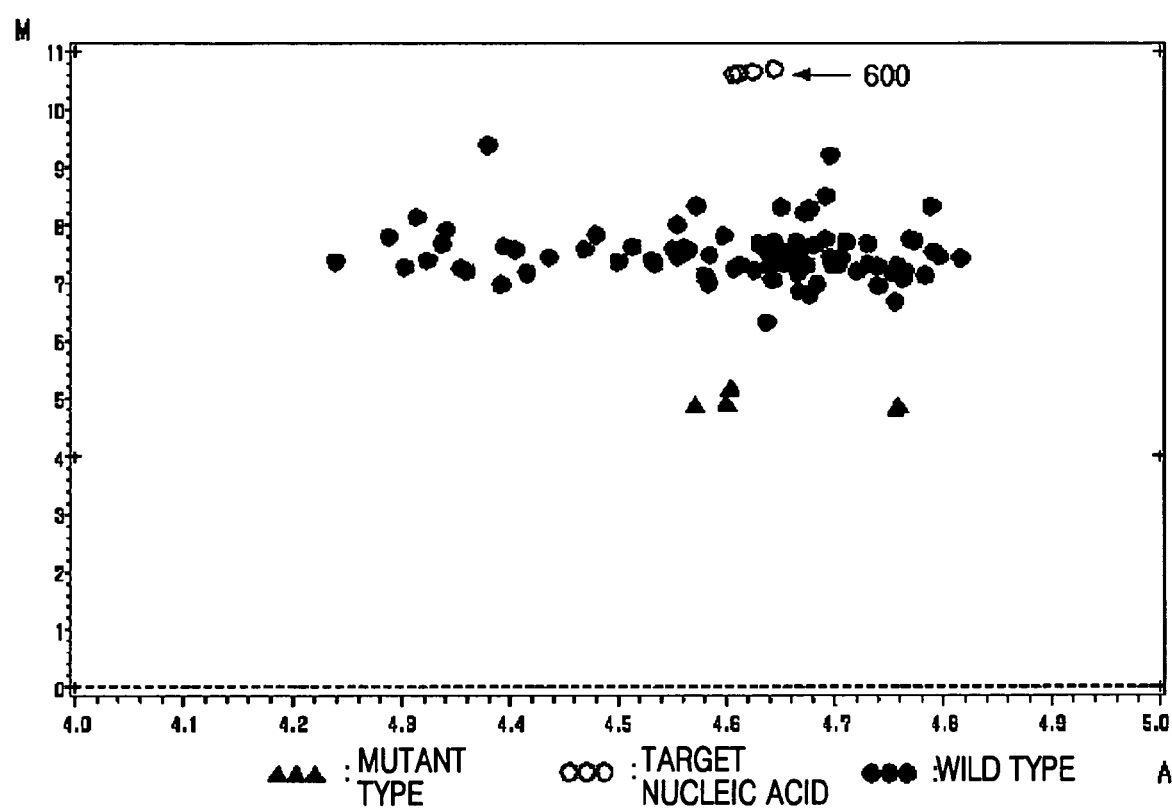
FIG. 6 is an MA plot used in setting up a genotyping algorithm for mutation site 13 of exon 1 (E01-13) of HNF-1α gene, in which the results of genotyping an unidentified target nucleic acid are also plotted.

FIG. 6 is an MA plot used in setting up a genotyping algorithm for mutation site 13 of exon 1 (E01-13) of HNF-1α gene, in which the results of genotyping an unidentified target nucleic acid are also plotted. The MA plot of FIG. 6 was obtained in the same manner as for the MA plot of FIG. 4. The genotyped results of the target nucleic acid are circled with reference numeral 600. It has to be determined whether the target nucleic acid is a wild type or a mutant type.

This genotyping process is performed as follows. Initially, ratio components m for the target nucleic acid that belong to circle 600 are substituted as input vectors into the genotyping algorithm with the estimated logistic regression coefficients a and b and the posterior probabilities that the target nucleic acid is a wild type or a mutant type are calculated as follows.

$$P(wild|m)=\exp(a+bm)/\{1+\exp(a+bm)\}$$

$$P(mutant|m)=1/\{1+\exp(a+bm)\}=1-P(wild|m)$$

The genotype of the target nucleic acid is determined according to the greater of the two posterior probabilities. It is preferable that provisional genotyping with the greater posterior probability is followed by reliability validation on the greater posterior probability at a particular significance level. In this case, if the reliability requirement is not met, genotyping of the target nucleic acid is deferred. In the reliability test, a confidence interval of the maximal posterior probability at the particular significance level is calculated. If the confidence interval includes 0.5, no genotyping of the target nucleic acid is performed and the target nucleic acid is assigned as a gray zone. A method of calculating the confidence interval of the greater posterior probability is described in detail in Chapter 1 of *Applied Logistic Regression* (Hosmer, D. W., Jr. and Lemeshow, S, John Wiley & Sons Inc., 1989), incorporated herein by reference in its entirety. Genotyping criteria may be more restricted by using a value that is greater than 0.5, for example, 0.7, in the reliability test. However, if the genotyping is deferred too frequently, then the DNA chip does not work properly. Therefore, it is required to establish optimal genotyping criteria in consideration of the no-call rate and the mis-call rate.

When there are a set of probes with the ratio components M that decrease with decreasing intensity components A, those ratio components are eliminated so that the remaining ratio components are used as a learning set. When a genotyping algorithm with logistic regression coefficients that are calculated using the learning set is used, genotyping of a target nucleic acid may be deferred if the result of hybridisation of the target nucleic acid is within an intensity domain with smaller ratio components.

Setting Up QC Basis for Amplicon Concentration and Applying the QC Basis

Since a probe specific to each amplicon is used in an embodiment of the present invention, whether each amplicon in a sample has been normally amplified can be checked before genotyping. Specifically, the genotyping method according to an embodiment of the present invention may further include setting up an amplicon concentration QC basis (operation 1000) before and after setting up a genotyping algorithm (operation 200) and applying the hybridization intensity of the target nucleic acid to the amplicon concentration QC basis (operation 1100) before and after genotyping a target nucleic acid (operation 300), to exclude a mutant amplicon which does not meet the QC requirements from the subject to be determined. Thus, the reliability of genotyping can be enhanced. A sample in which a target nucleic acid has not been amplified to a set-up concentration or more can be excluded from the subject to be analyzed.

The amplicon concentration QC basis may be set up using the following methods. In a first method, a confidence interval for the hybridization intensity of an amplicon to an ap is set up. Setting up the confidence interval includes the following procedures. To quantify degrees of amplification of amplicons having each mutation site, at least one ap candidate having a binding force within a specific range is selected through a thermodynamic simulation at a site in which mutation has not occurred. The selected at least one ap candidate is immobilized on the DNA chip and a standard nucleic acid is bound to the candidate to obtain a hybridization intensity between them. When quantifying the degrees of amplification using the ap probes, it is important that a signal obtained by scanning is in a linear interval, proportional to the number of fluorescent materials. If the signal intensity is too low, it is not clear whether it occurs due to low amplification of the nucleic acid. If the signal intensity is too high, the signal is present in a nonlinear interval or has the maximum value indicated by the scanner, and thus the hybridization intensity may not be accurately quantified. Thus, an ap which satisfies the above conditions and has the largest hybridization intensity is selected among a plurality of amplicon candidates for the respective amplicons. Then, only optimal probe sets selected are immobilized on a microarray to manufacture the DNA chip and a standard nucleic acid is reacted with the DNA chip to obtain hybridization intensity of the standard nucleic acid to each ap. The above process is repeated using a plurality of DNA chips, for example 50 DNA chips to obtain a mean or a median of the hybridization intensities. Then, an acceptable confidence interval is calculated from the mean or median value. For example, the acceptable confidence interval can be a mean/median−1.5 IQR~a mean/median+1.5 IQR, wherein IQR (inter quartile range) mean a difference between a first quartile which corresponds to 25% of the total data and a third quartile which corresponds to 75% of the total data when the total data is arranged in ascending order. In this meaning, a median corresponds to a second quartile. In a second method, a confidence interval for a ratio of the hybridization intensity of an amplicon to an ap is set up. Similarly in the first method, only optimal probe sets selected are immobilized on a microarray to manufacture the DNA chip, and a standard nucleic acid is reacted with the DNA chip to obtain a hybridization intensity of the standard nucleic acid to each ap. The hybridization intensity obtained by binding each amplicon to a relevant ap is summed up and the obtained sum is divided by the total number of ap probes, thus obtaining a mean value.

Then, a ratio is obtained by dividing the hybridization intensity to each ap by the above mean value. The above process is repeated, for example, in 30 times or more, the distribution of the ratios obtained for each ap is obtained. Next, an acceptable confidence interval is calculated based on the ratio distribution of the hybridization intensity an amplicon to each ap.

As described above, a genotyping method according to an embodiment of the present invention is robust to errors. Optimal probe sets for each mutation site in each amplicon are selected to minimize the probability of genotyping errors. In addition, input vectors for the genotyping algorithm are calculated using the H-L estimation, which is a statistical technique known to be robust to experimental errors, thereby minimizing the probability of genotyping errors. In an important test in which high accuracy is required, genotyping accuracy can be improved by applying more restricted genotyping criteria.

Chip's QC and QA are ensured with the genotyping method according to an embodiment of the present invention. Since a plurality of identical probes are immobilized on a chip used in the genotyping method according to an embodiment of the present invention, outlier data can be filtered out based on variations in data obtained from a plurality of identical probes. Also, criteria for screening failed chips can be established based on the experimental results obtained in a genotyping algorithm set-up process through repeated hybridization between wild type standard nucleic acids and ap probes.

Moreover, since an amplicon probe specific to each amplicon is used in the genotyping method according to an embodiment of the present invention, a sample in which an amplicon has not been amplified to a predetermined concentration can be excluded from the subject to be analyzed. Thus, the QA for the sample may be performed to increase the reliability of the analytical results of the genotype. Further, since an ap acts as a wild type probe at a plurality of mutation sites, genotyping may be performed at lower costs compared to a method in which a wild type probe is immobilized for each mutation site.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A genotyping method comprising
designing a plurality of probe sets for a mutation site of a target nucleic acid in an amplicon of the target nucleic acid, wherein a probe set consists of a discriminating probe and an amplicon probe, wherein the discriminating probe is a mutant type probe or a wild type probe for the mutation site, and the amplicon probe has a sequence which perfectly matches a region of the amplicon excluding any mutation site in the amplicon and that hybridizes to a sequence which is absent from other amplicons of the target nucleic acid;
immobilizing the plurality of probe sets on a substrate in order to manufacture an optimal probe set screening chip;
hybridizing a standard nucleic acid to the optimal probe set screening chip, wherein the standard nucleic acid is a wild type standard nucleic acid or a mutant type standard nucleic acid;
collecting quantitative hybridization intensity data;
calculating a value for each probe set of the following equation:

$$\{Mean(\ln(r^{wS}))-2SD(\ln(r^{wS}))/\sqrt{N^{wS}}\}-\{Mean(\ln(r^{HS}))+2SD(\ln(r^{HS}))/\sqrt{N^{HS}}\}$$

wherein N denotes a number of times hybridization of the standard nucleic acid has been performed;
$r^{wS}$ is a ratio between a hybridization intensity of a wild type standard nucleic acid to the amplicon probe and a hybridization intensity of the wild type standard nucleic acid to the discriminating probe;
$r^{HS}$ is a ratio between a hybridization intensity of a mutant type standard nucleic acid to the amplicon probe and a hybridization intensity of the mutant type standard nucleic acid to the discriminating probe; and
Mean and SD denote a mean value and a standard deviation, respectively, of N ln(r) values which are obtained by hybridizing the standard nucleic acid to the DNA chip N times; and
selecting the probe set having the largest value as the optimal probe set;
hybridizing a plurality of amplicons of a target nucleic acid to a DNA chip on which the optimal probe set for the mutation site is immobilized,
determining the genotype of the mutation site of the target nucleic acid, and
displaying the determined genotype to a user.

2. The genotyping method of claim 1, wherein at least two replicates of the optimal probe set for the mutation site are immobilized on the DNA chip.

3. The genotyping method of claim 2, wherein at least two spots of the discriminating probe are arranged side by side and at least two spots of the amplicon probe are arranged side by side on the DNA chip, and the spots of the amplicon probe are arranged adjacent to the spots of the discriminating probe.

4. The genotyping method of claim 1, further comprising:
(a) setting up a genotyping algorithm using data obtained from hybridization of a standard nucleic acid to the DNA chip; and
(b) genotyping the mutation site of the target nucleic acid by substituting an input vector that is calculated from hybridization of the amplicon to the DNA chip into the genotyping algorithm.

5. The genotyping method of claim 4, wherein (a) comprises:
(a-1) collecting quantitative hybridization intensity data obtained from hybridization of the standard nucleic acid to the DNA chip;
(a-2) calculating a ratio, $r_{ij}$, for every pairing of an amplicon probe ($ap_i$) of an optimal probe set (i) immobilized on the DNA chip and a discriminating probe ($dp_j$) of an optimal probe pair (j) immobilized on the DNA chip,
wherein the ratio, $r_{ij}$, is between a hybridization intensity of the standard nucleic acid to the amplicon probe ($ap_i$) and a hybridization intensity of the standard nucleic acid to the discriminating probe ($dp_j$), selecting the median from among the calculated ratios using Hodge-Lehman estimation, and
taking the logarithm of the median as a ratio component of a vector for the DNA chip; and
(a-3) repeating (a-1) and (a-2) with a plurality of DNA chips to obtain a set of vectors and setting up the genotyping algorithm using the set of vectors.

6. The genotyping method of claim 5, wherein (a-3) further comprises
calculating logistic regression coefficients for the set of vectors.

7. The genotyping method of claim 5, wherein (a-2) further comprises
calculating a product, $a_{ij}$, for every pairing of an amplicon probe ($ap_i$) of an optimal probe set (i) immobilized on the DNA chip and a discriminating probe ($dp_j$) of an optimal probe set (j) immobilized on the DNA chip,
wherein the product, $a_{ij}$, is calculated by multiplying the hybridization intensity of the standard nucleic acid to the amplicon probe ($ap_i$) and the hybridization intensity of the standard nucleic acid to the discriminating probe ($dp_j$);
selecting the median from among the calculated products using Hodge-Lehman estimation;
dividing the logarithm of the median by two to obtain an intensity component of the vector for the DNA chip;
the genotyping method further comprising
plotting a graph with the Y-axis parameterized by the ratio component and the X-axis parameterized by the intensity component before (a-3); and
the genotyping algorithm is set up in (a-3) using all of the ratio components if the ratio components are independent of the intensity components or using only ratio components which are independent of the intensity components if the ratio components are dependent on the intensity components.

8. The genotyping method of claim 5, wherein (a-2) further comprises
taking the larger of the hybridization intensity of the standard nucleic acid to the amplicon probe ($ap_i$) and the hybridization intensity of the standard nucleic acid to the discriminating probe ($dp_j$),
selecting the median from among the selected larger hybridization intensities using Hodge-Lehman estimation,
taking the logarithm of the median as an intensity component of a vector for the DNA chip;
the genotyping method further comprising
plotting a graph with the Y-axis parameterized by the ratio component and the X-axis parameterized by the intensity component before (a-3); and
the genotyping algorithm is set up in (a-3) using all of the ratio components if the ratio components are independent of the intensity components or using only ratio components which are independent of the intensity component if the ratio components are dependent on the intensity components.

9. The genotyping method of claim 5, further comprising
filtering out quantitative hybridization intensity data obtained from bad spots that have a larger diameter compared to an effective spot diameter from the quantitative hybridization intensity data collected in (a-1) before (a-2).

10. The genotyping method of claim 4, wherein (b) comprises:
   (b-1) collecting quantitative hybridization data obtained from hybridization of the amplicon to the DNA chip;
   (b-2) calculating a ratio, $r_{ij}$, for every pairing of an amplicon probe ($ap_i$) of an optimal probe set (i) immobilized on the DNA chip and a discriminating probe ($dp_j$) of an optimal probe pair (j) immobilized on the DNA chip, wherein the ratio, $r_{ij}$, is between a hybridization intensity of the amplicon to the amplicon probe ($ap_i$) and a hybridization intensity of the amplicon to the discriminating probe ($dp_j$),
   selecting the median from among the calculated ratios using the Hodge-Lehman estimation, and
   taking the logarithm of the median as an input vector for genotyping; and
   (b-3) substituting the input vector into the genotyping algorithm to genotype the target nucleic acid.

11. The genotyping method of claim 10, wherein (b-3) comprises
   calculating a posterior probability that the target nucleic acid is a wild type and a posterior probability that the target nucleic acid is a mutant type by substituting the input vector into the genotyping algorithm and
   determining the genotype of the target nucleic acid to be a wild type if the posterior probability that the target nucleic acid is a wild type is greater than the posterior probability that the target nucleic acid is a mutant type or determining the genotype of the target nucleic acid to be a mutant type if the posterior probability that the target nucleic acid is a wild type is less than the posterior probability that the target nucleic acid is a mutant type.

12. The genotyping method of claim 11, wherein (b-3) further comprises:
   validating the genotype determination based on a reliability requirement, wherein the reliability requirement is that the posterior probability of the determined genotype be at a predetermined significance level and
   deferring genotype determination of the target nucleic acid if the reliability requirement is not met.

13. The genotyping method of claim 10, further comprising
   filtering out quantitative hybridization intensity data obtained from bad spots that have a larger diameter compared to an effective spot diameter from the quantitative hybridization intensity data collected in (b-1) before (b-3).

14. The genotyping method of claim 4, further comprising, before (b),
   setting up a basis for sample quality control (QC) regarding whether each amplicon has been satisfactorily amplified, using the hybridization intensity of the standard nucleic acid to the amplicon probe obtained from the hybridization of the standard nucleic acid to the DNA chip; and applying the hybridization intensity of the amplicon to the amplicon probe obtained from hybridization of the amplicon to the DNA chip, to the QC basis to exclude an amplicon which fails the QC from determination of the genotype.

15. The genotyping method of claim 14, wherein the QC basis is a determination algorithm of amplicon concentration regarding whether the concentration of each amplicon in the sample is greater than a set-up value based on the data obtained from hybridization of the standard nucleic acid to the DNA chip, and
   the applying the hybridization intensity of the amplicon to the amplicon probe comprises
   determining the amplicon concentration by substituting an input vector that is calculated from data obtained from hybridization of the amplicon to the DNA chip into the determination algorithm and if the amplicon concentration is not more than the set-up value, excluding the amplicon from determination of the genotype.

16. The genotyping method of claim 4, further comprising
   correcting the genotyped results from (b) based on cross-hybridization data of the probe set for each mutation site.

17. A method of selecting an optimal probe set for a mutation site of a target nucleic acid, comprising:
   designing a plurality of probe sets for a mutation site of a target nucleic acid in an amplicon of the target nucleic acid,
   wherein a probe set consists of a discriminating probe for the mutation site and an amplicon probe, wherein the discriminating probe is a mutant type probe or a wild type probe for the mutation site, and the amplicon probe has a sequence which perfectly matches a region of the amplicon excluding any mutation site in the amplicon and that hybridizes to a sequence which is absent from other amplicons of the target nucleic acid;
   immobilizing the plurality of probe sets on a substrate in order to manufacture an optimal probe set screening chip;
   hybridizing a standard nucleic acid to the optimal probe set screening chip, wherein the standard nucleic acid is a wild type standard nucleic acid or a mutant type standard nucleic acid;
   collecting quantitative hybridization intensity data; and
   calculating a value for each probe set of the following equation:

$$\{\text{Mean}(\ln(r^{wS}))-2\text{SD}(\ln(r^{wS}))/\sqrt{N^{wS}}\}-\{\text{Mean}(\ln(r^{HS}))+2\text{SD}(\ln(r^{HS}))/\sqrt{N^{HS}}\}$$

wherein N denotes a number of times hybridization of the standard nucleic acid has been performed;
   $r^{wS}$ is a ratio between a hybridization intensity of a wild type standard nucleic acid to the amplicon probe and a hybridization intensity of the wild type standard nucleic acid to the discriminating probe;
   $r^{HS}$ is a ratio between a hybridization intensity of a mutant type standard nucleic acid to the amplicon probe and a hybridization intensity of the mutant type standard nucleic acid to the discriminating probe; and
   Mean and SD denote a mean value and a standard deviation, respectively, of N ln(r) values which are obtained by hybridizing the standard nucleic acid to the DNA chip N times; and
   selecting the probe set having the largest value as an optimal probe set.

* * * * *

SEQUENCE LISTING

```
<160> NUMBER OF SEQ ID NOS: 4

<210> SEQ ID NO 1
<211> LENGTH: 7
<212> TYPE: DNA
<213> ORGANISM: Homo sapiens

<400> SEQUENCE: 1 gccccct                                                              7

<210> SEQ ID NO 2
<211> LENGTH: 6
<212> TYPE: DNA
<213> ORGANISM: Homo sapiens

<400> SEQUENCE: 2 gcccct                                                               6

<210> SEQ ID NO 3
<211> LENGTH: 14
<212> TYPE: DNA
<213> ORGANISM: Artificial Sequence
<220> FEATURE:
<223> OTHER INFORMATION: discriminating primer

<400> SEQUENCE: 3
gaaggcccct ggac                                                      4

<210> SEQ ID NO 4
<211> LENGTH: 16
<212> TYPE: DNA
<213> ORGANISM: Artificial Sequence
<220> FEATURE:
<223> OTHER INFORMATION: amplicon primer

<400> SEQUENCE: 4
gctccgagga cgagac                                                    6
```